(12) United States Patent
Bovy et al.

(10) Patent No.: US 7,625,929 B2
(45) Date of Patent: *Dec. 1, 2009

(54) OXOPHENYL-CYCLOHEXYL-PROPANOLAMINE DERIVATIVES, PRODUCTION AND USE THEREOF IN THERAPEUTICS

(75) Inventors: Philippe R. Bovy, Mareil Marly (FR); Roberto Cecchi, Lodi (IT); Tiziano Croci, Milan (IT); Olivier Venier, Saint Mande (FR)

(73) Assignee: sanofi-aventis, Paris (FR)

( * ) Notice: Subject to any disclaimer, the term of this patent is extended or adjusted under 35 U.S.C. 154(b) by 414 days.

This patent is subject to a terminal disclaimer.

(21) Appl. No.: 10/515,093

(22) PCT Filed: May 26, 2003

(86) PCT No.: PCT/FR03/01579

§ 371 (c)(1),
(2), (4) Date: Nov. 19, 2004

(87) PCT Pub. No.: WO03/099819

PCT Pub. Date: Dec. 4, 2003

(65) Prior Publication Data

US 2005/0176731 A1  Aug. 11, 2005

(30) Foreign Application Priority Data

May 29, 2002 (FR) .................. 02 06560

(51) Int. Cl.
*A61K 31/445* (2006.01)
*C07D 211/06* (2006.01)
(52) U.S. Cl. ............... 514/330; 514/211.09; 514/230.5; 514/375; 514/651; 540/546; 546/226; 548/217
(58) Field of Classification Search ............ 514/211.09, 514/230.5, 330, 375, 651; 540/546; 546/226; 548/217
See application file for complete search history.

(56) References Cited

U.S. PATENT DOCUMENTS

| | | | | |
|---|---|---|---|---|
| 6,130,217 | A * | 10/2000 | Arnold et al. ............. | 514/253.1 |
| 6,770,645 | B2 * | 8/2004 | Denton et al. ................ | 514/242 |
| 2003/0040538 | A1 | 2/2003 | Miyoshi et al. ............. | 514/411 |
| 2004/0053916 | A1 * | 3/2004 | Bovy et al. ............. | 514/211.09 |

FOREIGN PATENT DOCUMENTS

| WO | WO 01/07026 | 2/2001 |
|---|---|---|
| WO | WO 01/44187 | 6/2001 |
| WO | WO 02/44139 | 6/2002 |

OTHER PUBLICATIONS

Arnold et al. "Preparation of . . . " CA 122:314571 (1995).*
Yoshida et al. "Obesity and . . . " Ca 117:109086 (1992).*
Furuya et al. "beta-3-Adrenergic . . . " CA 136:63350 (2001).*
Silverman "The organic chemicstry of drug design . . . " p. 72-73 ((1993).*
Martin et al. :beta-3-adrnoceptor agonists . . . Eur. Resp. J. v.7, p. 1610-1615 (1994).*
Strosberg "structure and function of the beta-3-adrenergic receptor" Ann. Rev. Pharmacol. Toxicol. v.37, p. 421-450 (1997).*
Braga et al. "Making crystals from . . . " chem. Commu. (2005) p. 3635-3645.*
Derwent Patent Abstract No. 200248 (2004).

* cited by examiner

*Primary Examiner*—Celia Chang
(74) *Attorney, Agent, or Firm*—Barbara E. Kurys

(57) ABSTRACT

The invention relates to the compounds of general formula (I)

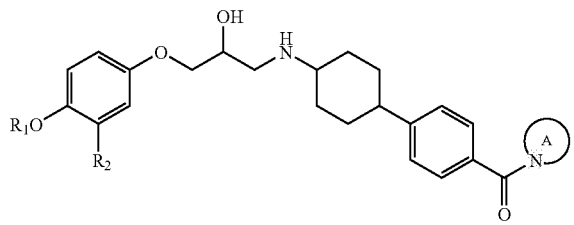

(I)

where $R_1$ represents H, a (C1-C4)alkyl, —CO(C1-C4)alkyl, (C1-C4)alkylphenyl or —CO-phenyl group, said phenyl being optionally substituted, $R_2$ represents H, a halogen atom, an —S(O)$_z$R$_3$, —NHSO$_2$R$_3$, —NHSO$_2$-phenyl or —NHSO$_2$—(C1-C4)alkylphenyl group where z is equal to 0, 1 or 2 and where $R_3$ represents a (C1-C4)alkyl group, said phenyl being optionally substituted;

A is chosen from

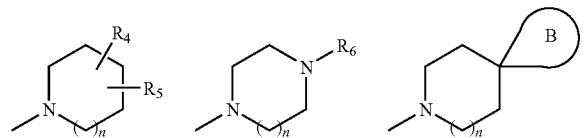

where n is equal to 0, 1 or 2, $R_4$ and $R_5$ represent H, a (C1-C4)alkyl, hydroxyl, cyano, phenyl, benzyl, piperidyl, —CONH$_2$, —CO-phenyl, —COOR$_3$, —CH(phenyl) (OH) and —C(phenyl)$_2$(OH) group, or $R_4$ and $R_5$ form together an optionally substituted 6-membered aromatic ring, $R_6$ represents H, a (C1-C4)alkyl, phenyl or benzyl group, and B represents a 5- or 6-membered nitrogen-containing heterocycle or homocycle optionally fused with a phenyl Group or optionally substituted; their addition salts; their method of preparation and their therapeutic application.

7 Claims, No Drawings

OXOPHENYL-CYCLOHEXYL-PROPANOLAMINE DERIVATIVES, PRODUCTION AND USE THEREOF IN THERAPEUTICS

The present invention relates to oxophenylcyclohexylpropanolamine derivatives, their preparation and their therapeutic application.

The present invention relates to compounds corresponding to formula (I):

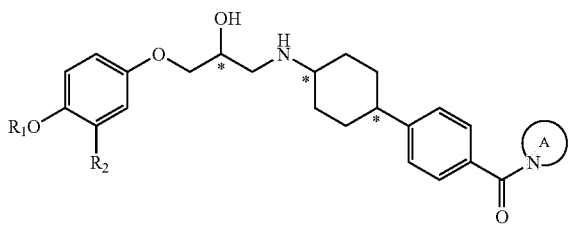

(I)

in which:
R$_1$ represents a hydrogen atom or a (C1-C4)alkyl group, a —CO(C1-C4)alkyl group, a (C1-C4)alkylphenyl group or a —CO-phenyl group, said phenyl being optionally substituted with one to three groups chosen independently of each other from halogen atoms, (C1-C4)alkyl and (C1-C4)alkoxy groups;

R$_2$ is chosen from one of the following groups:
a hydrogen atom,
a halogen atom,
an —S(O)$_z$R$_3$ group,
an —NHSO$_2$R$_3$ group,
an —NHSO$_2$-phenyl group, or
an —NHSO$_2$—(C1-C4)alkylphenyl group,
where z is equal to 0, 1 or 2 and where R$_3$ represents a (C1-C4)alkyl group, said phenyl being optionally substituted with one to three groups chosen independently from each other from halogen atoms, (C1-C4)alkyl and (C1-C4)alkoxy groups; and A is chosen from one of the groups of formula:

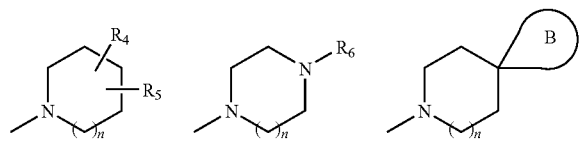

in which:
n is equal to 0, 1 or 2,
R$_4$ and R$_5$ are carried either by different carbon atoms, or by the same carbon atom of the ring to which they are attached, and are chosen independently of each other from the following groups: a hydrogen atom, a (C1-C4) alkyl, hydroxyl, cyano, phenyl, benzyl, piperidyl, —CONH$_2$, —CO-phenyl, —COOR$_3$ (where R$_3$ is as defined above), —CH(phenyl)(OH) and —C(phenyl)$_2$ (OH) group, at least one of R$_4$ or R$_5$ being different from a hydrogen atom, or R$_4$ and R$_5$ are carried by adjacent carbon atoms of the ring to which they are attached and form together with the carbon atoms carrying them a 6-membered aromatic ring optionally substituted with 1 to 3 (C1-C4)alkyl or (C1-C4)alkoxy groups, R$_6$ represents a hydrogen atom or a (C1-C4)alkyl, phenyl or benzyl group, and B represents a saturated or unsaturated, 5- or 6-membered cycloalkyl group optionally containing 1 or 2 nitrogen atoms, this cycloalkyl group being itself condensed with a phenyl group or substituted with one to three groups chosen from phenyl and carbonyl groups.

The compounds of formula (I) may contain one or more asymmetric carbon atoms. Moreover, the cyclohexyl group of these compounds has a geometric asymmetry. The signs * in formula (I) above denote carbons which can give rise to different geometric configurations.

The compounds of formula (I) can therefore exist in the form of enantiomers or diastereoisomers. These enantiomers, diastereoisomers, and mixtures thereof, including the racemic mixtures, form part of the invention.

Preference is given in particular to the compounds of formula (I) according to the invention which have the following configuration:

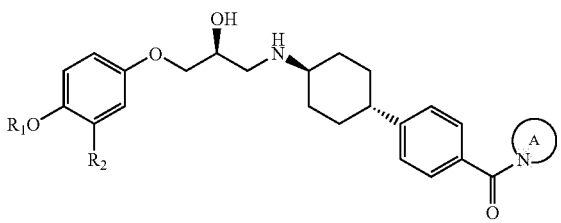

The compounds of formula (I) can exist in the form of bases or of addition salts with acids. Such addition salts form part of the invention.

These salts are advantageously prepared with pharmaceutically acceptable acids, but the salts of other acids useful for example for the purification or isolation of the compounds of formula (I) also form part of the invention.

The compounds of formula (I) can also exist in the form of hydrates or solvates, namely in the form of associations or combinations with one or more molecules of water or with a solvent. Such hydrates and solvates also form part of the invention.

In the context of the present invention, there is understood to mean by:
a halogen atom: a fluorine, a chlorine, a bromine or an iodine;
a (C1-C4)alkyl group: a linear or branched saturated aliphatic group comprising from 1 to 4 carbon atoms (it being of course understood that such a group can only be linear when it comprises less than 3 carbon atoms, and that such a group may be linear or branched when it comprises 3 or 4 carbon atoms). By way of examples, there may be mentioned methyl, ethyl, propyl, isopropyl, butyl and isobutyl groups, and the like;
a (C1-C4)alkoxy group: an —O—(C1-C4)alkyl radical where the (C1-C4)alkyl group is as defined above; and
a (C1-C4)alkylphenyl group: a group of formula —(CH$_2$)$_x$-phenyl where x is between 1 and 4.

Among the compounds of formula (I) which are the subject of the invention, there may be mentioned the preferred compounds in which:

$R_1$ represents a hydrogen atom;

and/or $R_2$ represents an —$SO_2R_3$ or —$NHSO_2R_3$ group where $R_3$ is as defined above ($R_3$ advantageously representing a methyl group or butyl group);

and/or A is chosen from one of the groups of formula:

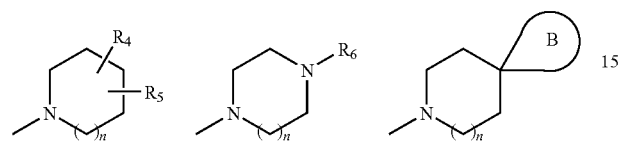

in which n is equal to 0 or 1, $R_4$, $R_5$, $R_6$ and B being as defined above.

Among the compounds of formula (I) which are the subject of the invention, other preferred compounds are those in which:

$R_1$ represents a hydrogen atom;

$R_2$ represents an —$SO_2R_3$ or —$NHSO_2R_3$ group, where $R_3$ is as defined above ($R_3$ advantageously representing a methyl group); and A is chosen from one of the following groups:

a group of formula

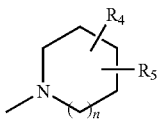

in which n is equal to 0 or 1 and $R_4$ and $R_5$ are carried either by different carbon atoms, or by the same carbon atom of the ring to which they are attached and are chosen independently of each other from the following groups: a hydrogen atom, a (C1-C4)alkyl, hydroxyl, cyano, phenyl, benzyl, piperidyl, —$CONH_2$, —CO-phenyl, —$COOR_3$ (where $R_3$ is as defined above), —CH(phenyl) (OH) and —C(phenyl)$_2$(OH) group, at least one of $R_4$ or $R_5$ being different from a hydrogen atom, a group of formula

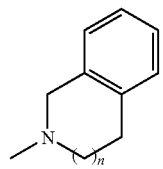

in which n is equal to 0 or 1 and the aromatic ring is optionally substituted with 1 to 3 groups chosen independently of each other from (C1-C4)alkyl and (C1-C4) alkoxy groups, a group of formula

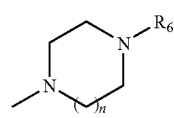

in which n is equal to 0 or 1 and $R_6$ represents a hydrogen atom or a benzyl group, and a group of formula

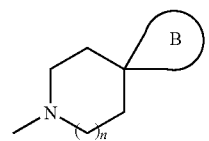

in which n is equal to 0 or 1 and B represents a saturated or unsaturated 5- or 6-membered cycloalkyl group optionally containing 1 or 2 nitrogen atoms, this cycloalkyl group being itself fused with a phenyl group or substituted with one to three groups chosen from phenyl and carbonyl groups.

In the text which follows, the expression protecting group Pg is understood to mean a group which makes it possible, on the one hand, to protect a reactive functional group such as a hydroxyl or an amine during synthesis and, on the other hand, to regenerate the intact reactive functional group at the end of synthesis. Examples of protecting groups and methods of protection and of deprotection are given in "Protective groups in Organic Synthesis", Green et al., $2^{nd}$ Edition (John Wiley & Sons, Inc., New York).

In accordance with the invention, the compounds of general formula (I) may be prepared according to the method described in scheme 1.

Scheme 1:

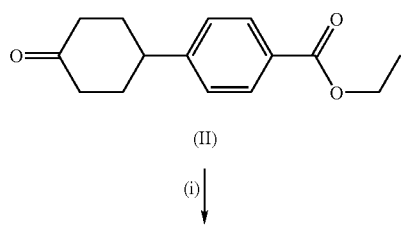

(II)

(i)

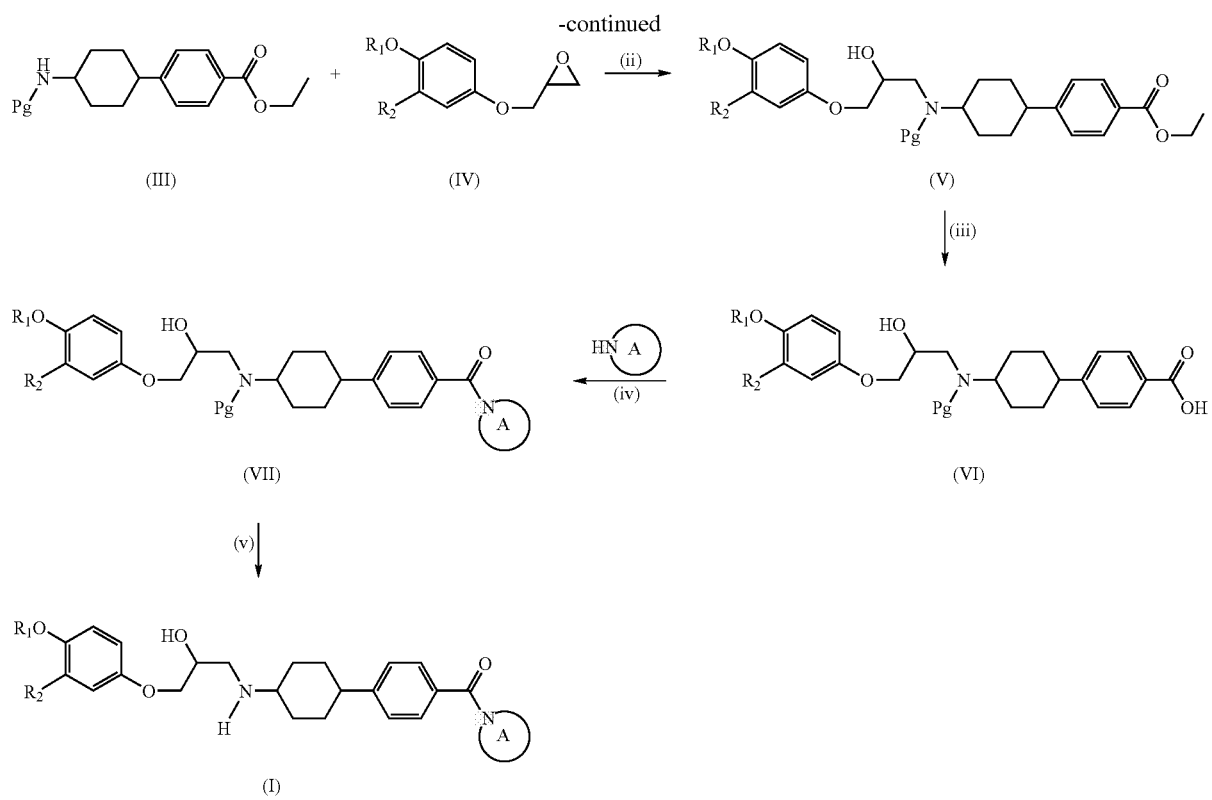

(III)  (IV)  (V)

(VII)  (VI)

(I)

According to scheme 1, the ketone functional group of the compound of formula (II) is converted in step (i) to an amine group according to methods well known to a person skilled in the art (for example by reductive amination). The amine (III) is partially protected with the aid of a protecting group Pg, such as an optionally substituted benzyl group (for example a para-methoxybenzyl group) or a methoxyethoxymethyl (MEM) group. It is preferable to use here protecting groups which only partially protect the reactivity of the amine functional group, that is to say which do not adversely affect its nucleophilic character. However, in the case where $R_2$ represents an $SOR_3$ group where $R_3$ is a (C1-C4)alkyl group, a compound (III) carrying a primary amine (Pg=H in scheme 1) will be preferably used as starting material.

In step (ii), the compound of formula (III) obtained at the end of step (i) is reacted with the epoxide of formula (IV), in which $R_1$ and $R_2$ are as defined above. The compounds of formula (IV) are known in the literature (for example in the patent application published under the number WO 02/44139) or may be prepared by methods similar to the methods described therein. In the case where $R_2$ can react during this step (ii) or subsequent steps, it is protected beforehand by means of protecting groups well known to persons skilled in the art.

During step (ii), in the case where the primary amine is partially protected in the compound (III), the compound (III) can only react with a single molecule of the epoxide (IV), and not with two molecules, thus avoiding the formation of reactive by-products.

Step (ii) leads to the amino alcohol of formula (V). This step is for example carried out in an organic solvent, such as a lower alcohol such as methanol, ethanol, isopropanol or tert-butanol, or in dimethyl sulfoxide, in a linear or cyclic ether, in an amide such as dimethylformamide or dimethylacetamide, or in a mixture of these solvents, preferably using at least equimolar quantities of the reagents. The reaction temperature is advantageously between room temperature and the reflux temperature of the chosen solvent.

When $R_1$ represents a hydrogen atom, it is preferable to protect the hydroxyl functional group with a protecting group in order to increase the yield of the reaction. To this effect, it is possible to use the customary protecting groups for phenol groups, such as methoxyethoxymethyl (MEM), trimethylsilylethoxymethyl (SEM), optionally substituted benzyl, or benzoyl.

In the case where $R_2$ represents an $SOR_3$ group where $R_3$ is a (C1-C4)alkyl group, the nitrogen of the compound (V) will be further protected with an amino-protecting group, such as t-butyloxycarbonyl (BOC) (Pg=BOC in scheme 1 for the compounds (V), (VI) and (VII)), according to methods known to persons skilled in the art.

In step (iii), the ethyl ester of the compound (V) obtained at the end of step (ii) is hydrolyzed to an acid (VI) by treating with a base, for example sodium hydroxide in a solvent or a mixture of solvents, such as an ethanol/water mixture.

The amide of formula (VII) is obtained in step (iv) by reacting the acid (VI) with an amine of formula:

in which A is defined in relation to formula (I) described above, in the presence of a coupling agent, for example 1-ethyl-3-(3-dimethylaminopropyl)carbodiimide (EDC), benzotriazol-1-yloxytris(dimethylamino)phosphonium hexafluorophosphate (BOP) or benzotriazol-1-yloxy-N,N'-tetramethyluronium tetrafluoroborate (TBTU), and in the presence of a base such as triethylamine or pyridine, in a solvent such as dichloromethane, acetonitrile or chloroform. It is also possible to activate the acid functional group of the compound (VI) in the form of an acid chloride or a carbonic anhydride, according to techniques known to persons skilled in the art.

The compounds of formula (I) are finally obtained, in step (v) after removing the protecting groups by means of techniques known to persons skilled in the art. In particular, when the protecting groups are benzyl groups, the deprotection is carried out by means of hydrogen in the presence of palladium on carbon, in a solvent such as ethanol. In scheme 1, it is of course understood that it is possible to use, as starting material (II), an ester other than an ethyl ester, for example a methyl or propyl ester or any other lower alkyl ester.

The preparation of the compounds of formula (II), which are useful for carrying out the method presented in scheme 1 above, may be carried out according to the method presented in scheme 2, illustrated by way of example for the preparation of an ethyl ester as compound (II).

According to scheme 2, the compound of formula (VIII) is condensed, in step (vi), with the compound of formula (IX), in which Hal represents a halogen atom, preferably bromine, for example according to the method described by MEYERS et al., in J. Org. Chem., 1974, 39, 2787. The intermediate alcohol of formula (X) thus obtained is converted, in step (vii), to an unsaturated compound (XI), for example with the aid of $SOCl_2$ in pyridine according to the method described by GONZALES-CAMENO et al., in Tetrahedron, 1994, 50, 10971 or with the aid of $POCl_3$, as described for example in Org. Prep. Proced. Int., 1995, 27, 122.

The unsaturated compound (XI) is then reduced, in step (viii), to a compound (XII) according to conventional methods, for example with the aid of hydrogen in the presence of palladium on carbon, in a solvent such as ethanol.

The hydrolysis of the acetal group of the compound (XII) is carried out, in step (ix), in a similar manner to the reaction described by SZANTAY et al. in Tetrahedron, 1996, 52(33), 11053, namely with the aid of hydrochloric acid in acetone, and leads to compound (XIII), which is then hydrolyzed to compound (II), in step (x), according to the method described by SEEBACH et al. in Synthesis Communications, 1982, 138 or by NELSON et al. in J. Org. Chem., 1994, 59(9), 2577. Alternatively, compound (XII) may be directly converted to compound (II) by heating under reflux in ethanol or by adding sulfuric acid, according to the method described by Scheme 2:

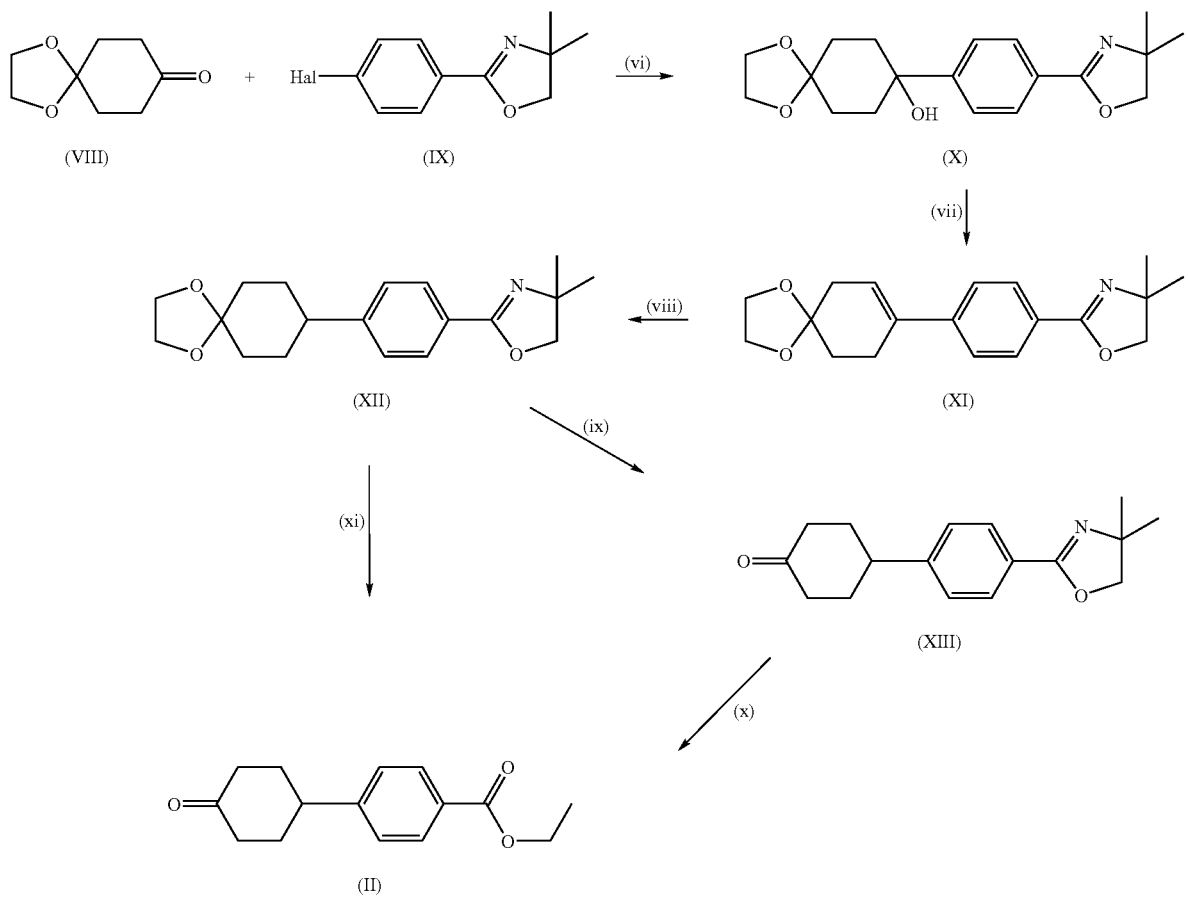

DEGRAW et al. in J. Med. Chem., 1992, 35(2), 320 or by TAYLOR et al. in Heterocycles, 1996, 43(2), 323.

It is of course understood that a method identical to that presented in scheme 2 could be carried out for the preparation of compounds (II) in the form of esters other than ethyl ester, by hydrolyzing compound (XII) with the aid of alcohols carrying alkyl groups different from an ethyl group.

In schemes 1 and 2, the starting compounds and the reagents, when their mode of preparation is not expressly described, are commercially available or are described in the literature, or may be prepared according to methods which are described therein or which are known to persons skilled in the art.

The following examples describe the preparation of certain compounds in accordance with the invention. These examples are not limiting and merely illustrate the present invention. The numbers for the compounds exemplified refer to those given in the table below, which illustrates the chemical structures and the physical properties of some compounds according to the invention.

PREPARATION 1 trans-4-[4-(benzyl{(2S)-3-[4-(benzyloxy)-3-[(methylsulfonyl)amino]phenoxy]-2-hydroxypropyl}amino)cyclohexyl]benzoic acid (Intermediate product of formula (VI) where $R_1$=Pg=benzyl and $R_2$=—NH—$SO_2$—$CH_3$)

1.1: ethyl trans-4-[4-(benzylamino)cyclohexyl]-benzoate

A solution of 8.51 ml of benzylamine (77.95 mmol) and of 16 g of ethyl 4-(cyclohexanone)-benzoate (64.96 mmol) in trimethyl orthoformate (192 ml) is heated for 18 h at 50° C. The solvents are evaporated under reduced pressure and 267 ml of ethanol are added, followed by 2.457 g of sodium borohydride. The reaction mixture is kept stirring for 2 h. The solvents are evaporated under reduced pressure and dichloromethane and water are added. The aqueous phase is extracted three times with dichloromethane. The organic phases are dried over magnesium sulfate and concentrated under reduced pressure. Ethyl trans-4-[4-(benzylamino)cyclohexyl]benzoate is obtained in the form of an oil (14.69 g, 67%) after purification on silica gel (eluent: ethyl acetate/ethanol 90/10). [M+H$^+$]=282.2

1.2: ethyl trans-4-[4-(benzyl{(2S)-3-[4-(benzyloxy)-3-[(methylsulfonyl)amino]phenoxy]-2-hydroxypropyl}amino)cyclohexyl]benzoate A mixture of 818 mg (1.82 mmol) of 4-benzyloxy-3-(N-tert-butoxycarbonyl-N-methylsulfonylamino)-1-((2S)-2,3-epoxypropoxy)benzene and 450 mg (1.82 mmol) of ethyl trans-4-[4-(benzylamino)cyclohexyl]benzoate in the form of a base is heated under reflux in 15 ml of absolute ethanol for 16 hours. The mixture is cooled, 3 ml of an ethanol solution saturated with hydrochloric acid are added thereto and the medium is heated at 50° C. for 6 hours. The solvent is evaporated and the medium is taken up in a mixture of 50 ml of a saturated sodium bicarbonate solution and 50 ml of ethyl acetate. The organic phase is washed with a saturated aqueous NaCl solution. The organic phase is dried, filtered and the solvent is evaporated under reduced pressure. The crude product is purified by chromatography on a silica gel column, eluting with a methylene chloride/methanol/NH$_4$OH (95/5/0.5) mixture. The title compound is obtained in the form of a white solid. [M+H$^+$]=687.

1.3: trans-4-[4-(benzyl{(2S)-3-[4-(benzyloxy)-3-[(methylsulfonyl)amino]phenoxy]-2-hydroxypropyl}amino)-cyclohexyl]benzoic acid A mixture of 4.48 g (5.71 mmol) of ethyl 4-{4-[benzyl((2S)-3-{4-(benzyloxy)-3-[(methylsulfonyl)-amino]phenoxy}-2-hydroxypropyl)amino]cyclohexyl}benzoate and 38 ml of a 1N aqueous sodium hydroxide solution in 114 ml of ethanol is heated at 50° C. overnight. The solvents are evaporated, the medium is taken up in water and a 1N hydrochloric acid solution is gently added to pH=1. The medium is filtered and dried under vacuum. The title compound (4.05 g, 94%) is thus obtained in the form of a white solid (melting point=160° C.).

PREPARATION 2 trans-4-[4-(benzyl{(2S)-3-[4-(benzyloxy)-3-(methylsulfonyl)phenoxy]-2-hydroxypropyl}amino)cyclohexyl]benzoic acid (Intermediate product of formula (IV) where $R_1$=Pg=benzyl and $R_2$=—$SO_2$—$CH_3$)

2.1: ethyl trans-4-[4-(benzyl{(2S)-3-[4-(benzyloxy)-3-(methylsulfonyl)phenoxy]-2-hydroxypropyl}amino)cyclohexyl]benzoate This product is obtained by carrying out the procedure as described in Preparation 1.2 above, using ethyl 4-[4-(benzylamino)cyclohexyl]benzoate and 4-benzyloxy-3-methylsulfonyl-1-((2S)-2,3-epoxypropoxy)benzene, described in patent application WO 99/65895, and without adding thereto the hydrochloric acid solution in ethanol. [M+H$^+$]=672.

2.2: trans-4-[4-(benzyl{(2S)-3-[4-(benzyloxy)-3-(methylsulfonyl)phenoxy]-2-hydroxypropyl}amino)cyclohexyl]benzoic acid The procedure is carried out in a manner similar to Preparation 1.3 above, but using ethyl 4-[4-(benzyl{(2S)-3-[4-(benzyloxy)-3-(methylsulfonyl)phenoxy]-2-hydroxypropyl}amino)cyclohexyl]benzoate. 8.13 g (93%) of the title compound are thus obtained in the form of a white solid (melting point=128-130° C.).

EXAMPLE 1 trans-N-[5-({(2S)-3-[(4-{4-[(4-benzylpiperidin-1-yl)carbonyl]phenyl}cyclohexyl)amino]-2-hydroxypropyl}oxy)-2-hydroxyphenyl]methanesulfonamide (compound No. 4)

1.1: N-[5-({(2S)-3-[benzyl(4-{4-[(4-benzylpiperidin-1-yl)carbonyl]phenyl}cyclohexyl)amino]-2-hydroxypropyl}oxy)-2-(benzyloxy)phenyl]methanesulfonamide A solution of 2 g (2.88 mmol) of trans-4-{4-[benzyl((2S)-3-{4-(benzyloxy)-3-[(methylsulfonyl)amino]phenoxy}-2-hydroxypropyl)amino]cyclohexyl}benzoic acid (Preparation 1), 0.78 g (5.76 mmol) of 1-hydroxybenzotriazole, 1.1 g (5.76 mmol) of 1-ethyl-3-(3-dimethylaminopropyl)carbodiimide, 1.2 ml of triethylamine and 1.01 ml (5.76 mmol) of 4-benzylpiperidine in a mixture of 26 ml of dichloromethane and 5 ml of acetonitrile is stirred for 24 hours. The solvents are evaporated under reduced pressure. Dichloromethane and water are added and the organic phase is washed three times with water. The organic phases are dried over magnesium sulfate and concentrated under reduced pressure. N-[5-({(2S)-3-[benzyl(4-{4-[(4-benzylpiperidin-1-yl)carbonyl]phenyl}-cyclohexyl)amino]-2-hydroxypropyl}oxy)-2-(benzyloxy)phenyl]methanesulfonamide is obtained in the form of a white solid (1.355 g, 57%) after purification on silica gel (eluent: dichloromethane/methanol 90/10). [M+H$^+$]=816.6.

1.2: trans-N-[5-({(2S)-3-[(4-{4-[(4-benzylpiperidin-1-yl)carbonyl]phenyl}cyclohexyl)amino]-2-hydroxypropyl}oxy)-2-hydroxyphenyl]methanesulfonamide A suspension of 1.35 g (1.65 mmol) of N-[5-({(2S)-3-[benzyl(4-{4-[(4-benzylpiperidin-1-yl)carbonyl]phenyl}cyclohexyl)amino]-2-hydroxy-propyl}oxy-2-(benzyloxy)phenyl]methanesulfonamide and of 0.77 g of palladium on carbon (10% Pd, 50% in water) in 130 ml of ethanol is placed under a hydrogen atmosphere and with stirring for 2 hours. The catalyst is then filtered and the solvents are evaporated under reduced pressure. The title compound is obtained in the form of a white solid (0.53 g) after purification on silica gel (eluent: gradient, dichloromethane/methanol/aqueous ammonia, 99/1/0.1 to 85/15/1.5).
Yield=50%; melting point=100-110° C.; [M+H$^+$]=636.6; $^1$H NMR (CDCl$_3$+D$_2$O, 300 MHz) : 1.1-2.05 (m, 14H), 2.02-2.18 (m, 3H), 2.45-2.7 (m, 5H), 2.7-2.9 (m, 2H), 2.95 (s, 3H), 3.7-3.95 (m, 3H), 4-4.1 (m, 1H), 4.6-4.8 (bm, 1H), 6.55 (dd, 1H), 7.0-7.3 (m, 9H).

EXAMPLE 2 trans-N-[2-hydroxy-5-({(2S)-2-hydroxy-3-[(4-{4-[(4-methylpiperidin-1-yl)carbonyl]phenyl}-cyclohexyl)amino]propyl}oxy)phenyl]methanesulfonamide (compound No. 3)
By carrying out the procedure as described in Example 1, using 4-methylpiperidine in step 1.1, the title compound (42 mg) is obtained in the form of a white solid.
Yield=16%; melting point=90-100° C.; [M+H$^+$]=560.4; $^1$H NMR (DMSO-D6, 300 MHz): 0.8-2.05 (m, 14H), 0.88 (d, 3H), 2.3-3 (m, 5H), 3.1-3.5 (m, 3H), 2.90 (s, 3H), 3.7-3.95 (m, 3H), 6.55 (dd, 1H), 6.7-6.82 (m, 3H), 7.18-7.32 (m, 4H).

EXAMPLE 3 trans-4-{[(2S)-2-hydroxy-3-({4-[4-({4-[hydroxy(phenyl)methyl]piperidin-1-yl}carbonyl)phenyl]-cyclohexyl}amino)propyl]oxy}-2-(methylsulfonyl)phenol (compound No. 9)
By carrying out the procedure described in Example 1, but using trans-4-[4-(benzyl{(2S)-3-[4-(benzyloxy)-3-(methylsulfonyl)phenoxy]-2-hydroxypropyl}amino)cyclohexyl]benzoic acid (Preparation 2) and phenyl(piperidin-4-yl)methanone in step 1.1, the title compound (20 mg) is obtained in the form of a white solid.

Yield=7.5%; melting point=120° C.; [M+H$^+$]=637; $^1$H NMR (DMSO-D6+D$_2$O, 500 MHz): 1-1.35 (m, 5H), 1.45 (dd, 2H), 1.65-1.85 (m, 4H), 1.95-2.05 (m, 2H), 2.45-2.56 (m, 2H), 2.6-2.7 (m, 1H), 2.75-2.8 (m, 1H), 2.82-2.95 (m, 1H), 3.19 (s, 3H), 3.45-3.6 (m, 1H), 3.8-3.9 (m, 3H), 4.28 (d, 1H), 4.3-4.45 (m, 1H), 6.88 (d, 1H), 7.1 (d, 1H), 7.12-7.2 (m, 10H).

EXAMPLE 4 trans-4-{[(2S)-3-({4-[4-(1,3-dihydro-2H-isoindol-2-ylcarbonyl)phenyl]cyclohexyl}amino)-2-hydroxypropyl]oxy}-2-(methylsulfonyl)phenol (compound No. 11)
By carrying out the procedure as described in Example 1, but using trans-4-[4-(benzyl{(2S)-3-[4-(benzyloxy)-3-(methylsulfonyl)phenoxy]-2-hydroxypropyl}amino)cyclohexyl]benzoic acid (Preparation 2) and isoindoline in step 1.1, the title compound is obtained (34 mg) in the form of a white solid.
Yield=14%; melting point=110° C.; [M+H$^+$]=565; $^1$H NMR (DMSO-D6+D$_2$O, 500 MHz): 1.23 (dd, 2H), 1.47 (dd, 2H), 1.82 (bd, 2H), 2 (bs, 2H), 2.49-2.58 (m, 1H), 2.6-2.7 (m, 1H), 2.75-2.8 (m, 1H), 3.19 (s, 3H), 3.8-3.95 (m, 3H), 4.76 (s, 2H), 4.83 (s, 2H), 6.9 (d, 1H), 7.22 (d, 1H), 7.19 (s, 1H), 7.2-7.4 (m, 6H), 7.5 (d, 2H).

EXAMPLE 5 trans-4-{[(2S)-3-({4-[4-(1,3-dihydro-1'H-spiro[indene-2,4'-piperidin]-1'-ylcarbonyl)phenyl]-cyclohexyl}amino)-2-hydroxypropyl]oxy}-2-(methylsulfonyl)phenol (compound No. 13)

By carrying out the procedure as described in Example 1, but using trans-4-[4-(benzyl{(2S)-3-[4-(benzyloxy)-3-(methylsulfonyl)phenoxy]-2-hydroxypropyl}amino)cyclohexyl]benzoic acid (Preparation 2) and 1,3-dihydrospiro[indene-2,4'-piperidine] in step 1.1, the title compound is obtained (79 mg) in the form of a white solid.
Yield=28%; melting point=125° C.; [M+H$^+$]=633; $^1$H NMR (DMSO-D6+D$_2$O, 500 MHz): 1.17-1.3 (m, 2H), 1.35-1.65 (m, 4H), 1.68-1.85 (m, 4H), 1.9-2.12 (m, 4H), 2.48-2.6 (m, 1H), 2.64-2.7 (m, 1H), 2.76-2.8 (m, 1H), 2.81-2.9 (m, 2H), 2.91-3.03 (m, 1H), 3.2 (s, 3H), 3.19-3.29 (m, 1H), 3.5-3.65 (m, 1H), 3.85-3.91 (m, 2H), 4.35-4.5 (m, 1H), 6.92 (d, 1H), 7.1-7.22 (m, 6H), 7.25-7.38 (m, 4H).

EXAMPLE 6 trans-4-{[(2S)-3-({4-[4-(2,3-dihydro-1'H-spiro[indene-1,4'-piperidin]-1'-ylcarbonyl)phenyl]-cyclohexyl}amino)-2-hydroxypropyl]oxy}-2-(methylsulfonyl)phenol (compound No. 15)

By carrying out the procedure as described in Example 1, but using trans-4-[4-(benzyl{(2S)-3-[4-(benzyloxy)-3-(methylsulfonyl)phenoxy]-2-hydroxy-propyl}amino)cyclohexyl]benzoic acid (Preparation 2) and 1'H-spiro[indene-1,4'-piperidine] in step 1.1, the title compound is obtained (68 mg) in the form of a white solid.
Yield=24%; melting point=125° C.; [M+H$^+$]=633; $^1$H NMR (DMSO-D6+D$_2$O, 500 MHz): 1.17-1.3 (m, 2H), 1.35-1.65 (m, 4H), 1.68-1.85 (m, 4H), 1.9-2.12 (m, 4H), 2.48-2.6 (m, 1H), 2.64-2.7 (m, 1H), 2.76-2.8 (m, 1H), 2.81-2.9 (m, 2H), 2.91-3.03 (m, 1H), 3.2 (s, 3H), 3.19-3.29 (m, 1H), 3.5-

3.65 (m, 1H), 3.79-3.85 (m, 1H), 3.85-3.91 (m, 1H), 4.37-4.5 (m, 1H), 6.92 (d, 1H), 7.1-7.22 (m, 6H), 7.25-7.38 (m, 4H).

EXAMPLE 7 trans-4-{[(2S)-3-({4-[4-(3,4-dihydro-1'H-spiro[naphthalene-1,4'-piperidin]-1'-ylcarbonyl)phenyl]cyclohexyl}amino)-2-hydroxypropyl]-oxy}-2-(methylsulfonyl)phenol (compound No. 17)

By carrying out the procedure as described in Example 1, but using trans-4-[4-(benzyl{(2S)-3-[4-(benzyloxy)-3-(methylsulfonyl)phenoxy]-2-hydroxypropyl}amino)cyclohexyl]benzoic acid (Preparation 2) and 3,4-dihydro-2H-spiro[naphthalene-1,4'-piperidine] in step 1.1, the title compound is obtained (93 mg) in the form of a white solid.

Yield=35%; melting point=125° C.; [M+H$^+$]=647; $^1$H NMR (DMSO-D6+D$_2$O, 500 MHz): 0.8-2.1 (m, 18H), 2.35-3 (m, 4H), 3.2 (s, 3H), 3.32 (bs, 1H), 3.62-3.95 (m, 5H), 4.25-4.5 (m, 1H), 6.9 (d, 1H), 6.9-7.52 (m, 10H).

The table which follows illustrates the chemical structures and the physical properties of some compounds according to the invention. In this table:

- in the "salt" column, "—" represents a compound in free base form,
- Me, Et, Ph and Bn represent methyl, ethyl, phenyl and benzyl groups, respectively.

TABLE

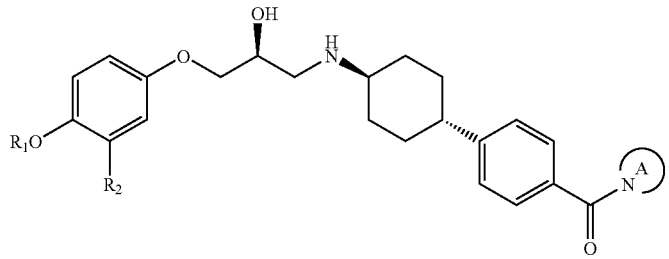

(I)

| No. | R$_1$ | R$_2$ | A | Salt | Melting point (° C.) |
|---|---|---|---|---|---|
| 1 | H | —NHSO$_2$CH$_3$ | piperidin-1-yl-4-COOEt | pamoate | 110-160 |
| 2 | H | —NHSO$_2$CH$_3$ | (2S)-1-methylpyrrolidin-2-yl-COOEt | pamoate | 110-150 |
| 3 | H | —NHSO$_2$CH$_3$ | 4-methylpiperidin-1-yl | — | 90-100 |
| 4 | H | —NHSO$_2$CH$_3$ | 4-benzylpiperidin-1-yl | — | 100-110 |
| 5 | H | —SO$_2$CH$_3$ | 4-benzylpiperidin-1-yl | — | 108-110 |
| 6 | H | —SO$_2$CH$_3$ | 4-methylpiperazin-1-yl | — | 85 |
| 7 | H | —SO$_2$CH$_3$ | piperazin-1-yl | — | 110 |

TABLE-continued (I)

[Structure: R₁O-(R₂-substituted phenyl)-O-CH₂-CH(OH)-CH₂-NH-(cyclohexyl)-(phenyl)-C(=O)-N(A)]

| No. | R₁ | R₂ | A | Salt | Melting point (°C) |
|---|---|---|---|---|---|
| 8 | H | —SO₂CH₃ | 4-carbamoyl-4-phenyl-1-methylpiperidine | — | 140 |
| 9 | H | —SO₂CH₃ | 4-(hydroxy(phenyl)methyl)-1-methylpiperidine | — | 120 |
| 10 | H | —NHSO₂CH₃ | 2-isoindolinyl | — | 100 |
| 11 | H | —SO₂CH₃ | 2-isoindolinyl | — | 110 |
| 12 | H | —SO₂CH₃ | 4-piperidinopiperidine | — | 75 |
| 13 | H | —SO₂CH₃ | 1'-methylspiro[indene-1,4'-piperidine] | — | 125 |
| 14 | H | —NHSO₂CH₃ | 1'-methylspiro[indane-1,4'-piperidine] | — | 140 |
| 15 | H | —SO₂CH₃ | 1'-methylspiro[indane-1,4'-piperidine] | — | 125 |

TABLE-continued

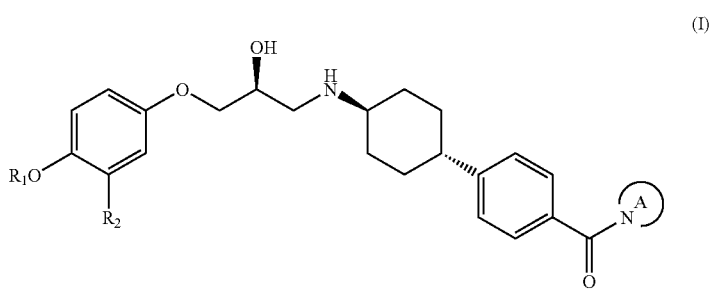

(I)

| No. | R₁ | R₂ | A | Salt | Melting point (°C.) |
|---|---|---|---|---|---|
| 16 | H | —NHSO₂CH₃ | N-linked spiro piperidine-tetrahydronaphthalene | — | 125 |
| 17 | H | —SO₂CH₃ | N-linked spiro piperidine-tetrahydronaphthalene | — | 125 |
| 18 | H | —NHSO₂CH₃ | N-piperidinyl-C(Ph)(Ph)OH | — | 135 |
| 19 | H | —SO₂CH₃ | N-piperidinyl-C(Ph)(Ph)OH | — | 140 |
| 20 | H | —NHSO₂CH₃ | N-piperidinyl-4-OH,4-Ph | — | 97 |
| 21 | H | —SO₂CH₃ | N-piperidinyl-4-OH,4-Ph | — | 100 |
| 22 | H | —SO₂CH₃ | N-piperidinyl-4-CN,4-Ph | — | 110 |
| 23 | H | —NHSO₂CH₃ | 6,7-dimethoxy-1,2,3,4-tetrahydroisoquinolin-2-yl | — | 126 |
| 24 | H | —SO₂CH₃ | 6,7-dimethoxy-1,2,3,4-tetrahydroisoquinolin-2-yl | — | 112 |

TABLE-continued (I)

| No. | $R_1$ | $R_2$ | A | Salt | Melting point (° C.) |
|---|---|---|---|---|---|
| 25 | H | —SO$_2$CH$_3$ | | — | 135 |

The compounds according to the invention have been the subject of pharmacological trials which make it possible to determine their agonist activity effect against beta-3 receptors.

The agonist activity against beta-3 receptors (indicated by the production of cAMP induced by the test compound) was studied with the aid of membrane preparations of SKNMC cells (human neuroblastoma cells) in the presence of selective beta-1 and beta-2 antagonists (CGP20712 and ICI118551, both at a concentration of $10^{-6}$M). The activity of the compounds according to the invention (pKa) is greater than or equal to 6.0 (it is in general between 6.0 and 7.6). Their efficacy is greater than or equal to 60% and is generally in the range from 60 to 90%.

The activities of the compounds according to the invention toward the beta-1 and beta-2 receptors were studied on the atrium and on the trachea, respectively, of guinea pigs. The agonist and antagonist activities were measured. It was thus found that the compounds according to the invention are selective toward the beta-3 receptors: indeed, they are at least 50 times more active toward the beta-3 receptors than toward the beta-1 or beta-2 receptors.

The compounds according to the invention may therefore be used for the preparation of medicaments intended in particular for the treatment of diseases in which the beta-3 receptors are involved. More particularly, the compounds according to the invention may be used as medicaments with agonist beta-3 action.

Thus, according to another of its aspects, the subject of the invention is a medicament which comprises a compound of formula (I), or an addition salt thereof with a pharmaceutically acceptable acid, or a hydrate or a solvate of the compound of formula (I).

Examples of diseases in which the beta-3 receptors are involved are abundantly described in the literature. The compounds of formula (I), and their pharmaceutically acceptable salts, or hydrates or solvates of these compounds, can therefore be indicated for the treatment of gastrointestinal diseases such as inflammatory bowel diseases, for example irritable bowel syndrome (IBS) or inflammatory bowel disease (IBD), as modulators of intestinal motility, as lipolytics, anti-obesity, anti-diabetic, anti-glaucomatous and cicatrizing agents, as uterine contraction inhibitors, as tocolytics for preventing or delaying preterm labor, and for the treatment and/or prophylaxis of dysmenorrhea. In addition, the compounds of formula (I), and their pharmaceutically acceptable salts, or hydrates or solvates of these compounds, may be used in the treatment of certain diseases of the central nervous system, for example as psychotropics or antidepressants, and certain disorders of the urinary tract, such as urinary incontinence.

The present invention, according to another of its aspects, also relates to a method for treating the pathologies indicated above which comprises the administration, to a patient, of an effective dose of a compound according to the invention, or one of its pharmaceutically acceptable salts, or a hydrate or solvate of this compound.

The present invention also relates to pharmaceutical compositions comprising, as active ingredient, at least one compound according to the invention. These pharmaceutical compositions contain an effective dose of a compound according to the invention, or a pharmaceutically acceptable salt, a hydrate or solvate of said compound, and at least one pharmaceutically acceptable excipient.

Said excipients are chosen, according to the pharmaceutical dosage form and the desired mode of administration, from the usual excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, may be administered in unit form for administration, as a mixture with conventional pharmaceutical excipients, to animals and to human beings for the prophylaxis or treatment of the above disorders or diseases.

The appropriate unit forms for administration comprise the oral forms such as tablets, soft or hard gelatin capsules, powders, granules and oral solutions or suspensions, the forms for sublingual, oral, intratracheal, intraocular or intranasal administration or for administration by inhalation, the forms for topical, transdermal, subcutaneous, intramuscular or intravenous administration, the forms for rectal administration and implants. For topical application, the compounds according to the invention may be used in creams, gels, ointments or lotions.

The dose of active ingredient administered is between 0.01 and 20 mg per kilo of body weight of the mammal to be treated, preferably between 0.1 and 10 mg/kg. In humans, the dose may vary from 0.5 mg to 1500 mg per day, for example from 2.5 to 500 mg according to the age of the subject to be treated, the type of treatment (prophylactic or curative) and the seriousness of the condition. The compounds of formula (I) are generally administered in unit dosage form of 0.1 to 500 mg, preferably 0.5 to 100 mg of active ingredient, between one and five times per day.

There may be particular cases where higher or lower dosages are appropriate; such dosages do not depart from the scope of the invention. According to the usual practice, the dosage appropriate for each patient is determined by the doctor according to the mode of administration, the weight and the response of said patient.

The invention claimed is:

1. A compound corresponding to formula (I):

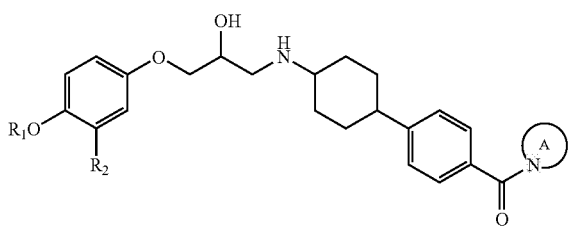

(I)

wherein:
$R_1$ is a hydrogen atom;
$R_2$ is an —S(O)$_z$R$_3$ group, or an —NHSO$_2$R$_3$ group,
where z is equal to 2 and where $R_3$ is a (C1-C4)alkyl group; and
A is

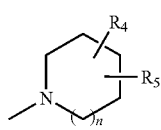

wherein:
n is equal to 0, 1 or 2, and
$R_4$ and $R_5$ are carried either by different carbon atoms, or by the same carbon atom of the ring to which they are attached, and are chosen independently of each other from the following groups: a hydrogen atom, a (C1-C4) alkyl, hydroxyl, cyano, phenyl, benzyl, piperidyl, —CONH$_2$, —CO-phenyl, —COOR$_3$ (where $R_3$ is as defined above), —CH(phenyl)(OH) and —C(phenyl)$_2$(OH) group, at least one of $R_4$ or $R_5$ being different from a hydrogen atom,
or $R_4$ and $R_5$ are carried by adjacent carbon atoms of the ring to which they are attached and form together with the carbon atoms carrying them a 6-membered aromatic ring optionally substituted with 1 to 3 (C1-C4)alkyl or (C1-C4)alkoxy groups,
or an addition salt with acid thereof.

2. The compound according to claim 1 wherein A is

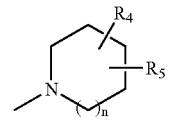

wherein n is equal to 0 or 1 and $R_4$ and $R_5$ are carried either by different carbon atoms, or by the same carbon atom of the ring to which they are attached and are chosen independently of each other from the following groups: a hydrogen atom, a (C1-C4)alkyl, hydroxyl, cyano, phenyl, benzyl, piperidyl, —CONH$_2$, —CO-phenyl, —COOR$_3$ (where $R_3$ is as defined in claim 1), —CH(phenyl)(OH) and —C(phenyl)$_2$(OH) group, at least one of $R_4$ or $R_5$ being different from a hydrogen atom,
or an addition salt with acid thereof.

3. A process for preparing the compound of formula (I) according to claim 1 comprising reacting a compound of formula (VI), in which $R_1$ and $R_2$ are as defined in claim 1 and Pg is a protecting group:

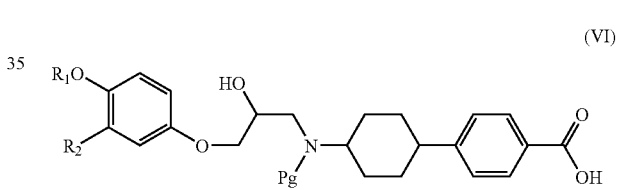

(VI)

with an amine of formula:

in which A is as defined in claim 1, in the presence of a coupling agent and a base, and then removing the protecting group Pg from the product thus obtained.

4. A pharmaceutical composition comprising a compound of formula (I) according to claim 1 or a pharmaceutically acceptable salt thereof, at least one pharmaceutically acceptable excipient.

5. A pharmaceutical composition comprising a compound of formula (I) according to claim 2 or a pharmaceutically acceptable salt therefore, and at least one pharmaceutically acceptable excipient.

6. A method for the treatment of diabetes which comprises administering to a patient in need of such treatment an effective amount of a compound according to claim 1.

7. A method for the treatment of diabetes which comprises administering to a patient in need of such treatment an effective amount of a compound according to claim 2.

* * * * *